(12) United States Patent
Verswyvel et al.

(10) Patent No.: US 11,066,503 B2
(45) Date of Patent: Jul. 20, 2021

(54) VERY SOFT, NON-STICKY AND TRANSPARENT STYRENIC THERMOPLASTIC ELASTOMER COMPOSITION

(71) Applicant: INEOS STYROLUTION GROUP GMBH, Frankfurt am Main (DE)

(72) Inventors: Michiel Verswyvel, Mechelen (BE); Norbert Niessner, Friedelsheim (DE); Eike Jahnke, Aubonne (CH); Daniel Wagner, Bad Duerkheim (DE); Konrad Knoll, Mannheim (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 157 days.

(21) Appl. No.: 16/492,768

(22) PCT Filed: Mar. 12, 2018

(86) PCT No.: PCT/EP2018/056045
§ 371 (c)(1),
(2) Date: Sep. 10, 2019

(87) PCT Pub. No.: WO2018/166958
PCT Pub. Date: Sep. 20, 2018

(65) Prior Publication Data
US 2020/0071446 A1 Mar. 5, 2020

(30) Foreign Application Priority Data
Mar. 16, 2017 (EP) ..................... 17161349

(51) Int. Cl.
| | | |
|---|---|---|
| C08F 293/00 | (2006.01) | |
| C08F 297/04 | (2006.01) | |
| A61L 29/06 | (2006.01) | |
| A61L 29/12 | (2006.01) | |
| A61L 29/14 | (2006.01) | |
| C08K 5/01 | (2006.01) | |
| C08K 5/09 | (2006.01) | |
| C08K 5/11 | (2006.01) | |

(52) U.S. Cl.
CPC .......... *C08F 297/044* (2013.01); *A61L 29/06* (2013.01); *A61L 29/126* (2013.01); *A61L 29/141* (2013.01); *C08K 5/01* (2013.01); *C08K 5/09* (2013.01); *C08K 5/11* (2013.01)

(58) Field of Classification Search
CPC ......... C08F 297/044; C08K 5/01; C08K 5/09; C08K 5/11; C08L 53/02
See application file for complete search history.

(56) References Cited

U.S. PATENT DOCUMENTS

| | | |
|---|---|---|
| 6,031,053 A | 2/2000 | Knoll et al. |
| 6,197,889 B1 | 3/2001 | Knoll et al. |
| 6,521,712 B1 | 2/2003 | Knoll et al. |
| 6,593,430 B1 | 7/2003 | Knoll et al. |
| 6,673,857 B1 | 1/2004 | Knoll et al. |
| 2009/0286918 A1 | 11/2009 | Stewart et al. |
| 2014/0011929 A1 | 1/2014 | Knoll et al. |

FOREIGN PATENT DOCUMENTS

| | | | |
|---|---|---|---|
| WO | 2012/055919 A1 | 5/2012 | |
| WO | WO2012055919 A1 * | 5/2012 | ............ C08F 297/04 |
| WO | 2012/084914 A1 | 6/2012 | |

\* cited by examiner

*Primary Examiner* — Robert S Jones, Jr.
(74) *Attorney, Agent, or Firm* — J.A. Lindeman & Co. PLLC

(57) ABSTRACT

Thermoplastic elastomer compositions can be used for medical skin contact applications, comprising: a) 90.9 to 69.0 wt.-% star-shaped block copolymer A with 4 arms of the general structure $[S_1—(S/B)_k—(S/B)_l—(S/B)_m—S_2]_n—X$, where $S_1$ and $S_2$ are vinylaro-matic hard polymer and S/B are soft random vinylaromatic/diene copolymer blocks; X is a coupling center; and b) 9.1 to 31.0 wt.-% of a plasticizer B: b1) a mixture of mineral oil B1 and cyclohexane 1,2-dicarboxylic acid $C_8$ to $C_{10}$ dialkyl ester B2; or b2) a mixture of mineral oil B1 and vegetable oil B3.

22 Claims, No Drawings

VERY SOFT, NON-STICKY AND TRANSPARENT STYRENIC THERMOPLASTIC ELASTOMER COMPOSITION

The invention relates to styrenic thermoplastic elastomers (S-TPE), to soft thermoplastic elastomer compositions comprising said elastomers and the use for the production of flexible or elastic moldings, and further the use of said moldings, in particular for medical applications.

Common thermoplastic elastomers used for medical applications such as plasticized PVC have several disadvantages. PVC is a rather polar polymer and it therefore requires a rather polar plasticizer (e.g. phthalates). When joining soft medical tubes made from PVC with fittings made from stiff styrenic polymers, often plasticizer migration of these more polar plasticizers from the PVC parts into the styrenic parts occurs. This migration destroys the plastic properties and results in reduced environmental stress-cracking resistance. Thus, for medical applications there is an interest to avoid typical PVC plasticizers. In particular for medical skin-contact applications there is a need in thermoplastic elastomeric materials which allow food approved plasticizers without influence on human hormonal regulation.

U.S. Pat. Nos. 6,031,053 and 6,197,889 disclose elastomeric linear and star-shaped SBC block copolymers i.a. of the general formula Y—[(A—B/A)$_n$—A]$_{m+1}$ and Y—[(B/A—A)$_n$]$_{m+1}$ where A is a vinylaromatic block forming a hard phase, B/A is a random diene/vinylaromatic copolymer block forming a soft phase, Y is a radical of a coupling agent, m and n are 1 to 10. Examples show coupled star shaped block copolymers of the structure Y—[(B/A)—(B/A)—(B/A)—A] having a molecular weight Mw of 175000 g/mol or 145000 g/mol.

WO 2012/055919 describes star-shaped elastomeric SBC block copolymers having at least 2 different arms and mixtures thereof. Preferred are coupled block copolymers having 3 or 4 arms—having a hard-soft-hard-soft-hard pentablock character—of the general formula [A1—B/A—A2—]$_m$[A2—]$_l$Y where A1 and A2 are vinylaromatic hard blocks (A1 greater than A2) and B/A is a soft vinylaromatic/diene copolymer block. For several applications the afore-mentioned elastomeric SBC block copolymers are too hard. In order to reduce the hardness, the use of a plasticizer oil with a higher polarity than medical white oil but lower than familiar PVC plasticizers has been proposed.

U.S. Pat. No. 6,673,857 discloses a thermoplastic elastomer composition comprising 5 to 99 wt.-% of a SBC blockcopolymer and 1 to 95 wt.-%, preferably 4 to 49 wt.-%, of a plasticizer based on vegetable oil or its mixture with white oil.

The SBC blockcopolymer is a symmetrical three-block copolymer or a star block copolymer with outer blocks S and random soft blocks B/S lying therebetween (no examples). Compositions with linear S-B/S-S block copolymers (Mw 163.000 g/mol) and 5 or 10 wt.-% of a white oil/sunflower oil mixture (40/60) have a shore A hardness of 68 or 63 and a high melt flow (5 kp, 10 min−1) of 16.9 or 27.8 at 180° C.

These thermoplastic elastomer compositions leave something desired in terms of their processability. Moreover, their softness—without bleeding of the plasticizer oil—is in need of improvement.

WO 2012/084914 describes thermoplastic elastomer compositions comprising a) 5% to 99 wt.-% of a block copolymer synthesized from hard blocks A of vinylaromatic monomers and one or more random soft blocks B of diene/vinylaromatic copolymers, and b) 1% to 95 wt.-% of a plasticizer, in particular mixtures of diisononyl cyclohexane-1,2-dicarboxylate (DINCH) with white oil. The block copolymer is preferably a symmetrical triblock copolymer with external blocks A and an inner block B. With said plasticizer combination the oil uptake of said triblock copolymer could be increased to 50 wt.-% and the softness improved, but the mechanical properties of this material are not satisfying for many applications.

Thus, there is a need for improved materials which are suitable for medical applications and which do not have the afore-mentioned disadvantages.

One object of the invention is to provide transparent S-TPEs which, in comparison to prior art S-TPE, have a satisfying oil-uptake but without negative effects on the mechanical properties. Thus, it is an object to provide a S-TPE composition which is very soft—without or at least reduced bleeding of the plasticizer—while good mechanical properties (e.g. E-modulus, stress at break and strain at break) are maintained. One further object of the invention is that S-TPEs with the afore-mentioned properties are provided which can be produced in a high space-time yield. One further object of the invention is to provide a S-TPE composition which maintains a good processability—identified by a melt volume flow rate (MFI$_{200/5}$) of 16 cm$^3$/10 min or less—when increasing amounts of plasticizers are added.

One aspect of the invention is a thermoplastic elastomer composition comprising (or consisting of) components a), b) and c):

a) 90.9 to 69.0 wt.-% of at least one star-shaped block copolymer A of the structure

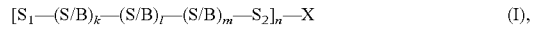

$$[S_1-(S/B)_k-(S/B)_l-(S/B)_m-S_2]_n-X \quad (I),$$

where $S_1$ and $S_2$ are polymer blocks made from at least one vinylaromatic monomer and S/B are random copolymer blocks made from at least one vinylaromatic monomer and at least one diene forming a soft phase; X is a coupling center derived from a polyfunctional (di- or multi-functional) coupling agent;

b) 9.1 to 31.0 wt.-% of a plasticizer B; and
c) 0 to 2.0 wt.-% of further additives C;
wherein the sum of components a), b) and c) is 100 wt.-%;
the arms $S_1-(S/B)_k-(S/B)_l-(S/B)_m-S_2$ are identical;
the proportion of the blocks $S_1$ and $S_2$ (forming a hard phase), based on the entire block copolymer A, is from 24 to 40 wt.-%;
the vinylaromatic monomer/diene (=S/B) ratio of all of the blocks (S/B) is from 1/0.45 to 1/2.5;
the S/B-ratio of the blocks $(S/B)_k$, $(S/B)_l$ and $(S/B)_m$ is different from each other; the S/B-ratio of the blocks $(S/B)_k$ and $(S/B)_m$ is lower than the S/B-ratio of the block(s) $(S/B)_l$;
the weight ratio of blocks S2/S1 is from 0.1 to 0.8; and
the weight average molar mass $M_w$ (determined by GPC according to ISO 16014-3:2012) of the block copolymer A is from 220.000 to 450.000 g/mol; n is a natural number from 1 to 8; k, m are 1; and l is a natural number of at least 1; and
the plasticizer B is
 b1) a mixture composed of mineral oil B1 and at least one cyclohexane 1,2-dicarboxylic acid $C_8$ to $C_{10}$ dialkyl ester B2; or
 b2) a mixture composed of mineral oil B1 and at least one vegetable oil B3 having a iodine value (g/100 g) of no more than 130.

The melt volume flow rate (=MFI, measured on a polymer melt at 200° C. and 5 kg load according to ISO 1133-1:2011) of the thermoplastic elastomer composition according to the invention generally is in the range of from 8 to 16 cm³/10 min, preferably 9 to 15 cm³/10 min, more preferably 10 to 12 cm³/10 min.

The Shore A hardness of the thermoplastic elastomer composition—determined in accordance with ASTM D2240 (measurement after 15 seconds)—is at most 70, preferably in the range of from 35 to 65, more preferably in the range of from 40 to 60.

High space-time yield means the time between the addition of the first monomer until the addition of the terminator is 3.5 hours or less.

In the context of the invention, the average molar mass Mw is determined by GPC according to ISO 16014-3:2012 (Low T<60° C. size exclusion with relative calibration method against polystyrene standards in THF).

Wt.-% means percent by weight.

In the context of the invention "diene" means a conjugated diene. Butadiene means 1,3-butadiene.

If in the thermoplastic elastomer composition according to the invention optional component (c) is present, its minimum fraction is customarily 0.01 wt.-%.

Preferably the thermoplastic elastomer composition according to the invention consists of components a), b) and c).

Often the thermoplastic elastomer composition comprises (or consists of) components a), b) and c) in the following amounts:
a) 87.0 to 69.0 wt.-%;
b) 13.0 to 31.0 wt.-%;
c) 0 to 2.0 wt.-%.

According to one preferred embodiment—in particular for applications requiring softness (without bleeding of the plasticizer), a high stress at break and a good strain at break—the thermoplastic elastomer composition according to the invention comprises 9.1 to 20.0 wt.-%, more preferably 13.0 to 20.0 wt.-%, of plasticizer B (component b)), in particular mixture b2), and the Mw of block copolymer A is 250000 to 320000 g/mol.

According to a further preferred embodiment—in particular for applications requiring extreme softness (without bleeding of the plasticizer), a good stress at break and a high strain at break—the thermoplastic elastomer composition according to the invention comprises more than 20 wt.-%, in particular 21 to 31.0 wt.-% of plasticizer B (component b)), in particular mixture b2), and the Mw of block copolymer A is 325000 to 410000 g/mol.

The thermoplastic elastomer composition according to the invention preferably comprises as component a) one star-shaped block copolymer A.

A further subject of the invention is the novel star-shaped block copolymer A used as component a) in the thermoplastic elastomer composition according to the invention described above.

Component a)

Star-shaped block copolymer A is of the structure:

$$[S_1-(S/B)_k-(S/B)_l-(S/B)_m-S_2]_n-X \qquad (I)$$

where $S_1$ and $S_2$ are polymer blocks made from at least one, preferably one, vinylaromatic monomer and S/B are random copolymer blocks made from at least one, preferably one, vinylaromatic monomer, and at least one, preferably one, diene, forming a soft phase; X is a coupling center derived from a polyfunctional coupling agent;
wherein the arms $S_1-(S/B)_k-(S/B)_l-(S/B)_m-S_2$ are identical;

the proportion of the blocks $S_1$ and $S_2$ (forming a hard phase)—based on the entire block copolymer A—is from 24 to 40 wt.-%;
the vinylaromatic monomer/diene (=S/B) weight ratio of all of the blocks (S/B) is from 1/0.45 to 1/2.5, preferably from 1/0.50 to 1/1.2;
the S/B-ratio of the blocks $(S/B)_k$, $(S/B)_l$ and $(S/B)_m$ is different from each other; the S/B-ratio of the blocks $(S/B)_k$ and $(S/B)_m$ is lower than the S/B-ratio of the block(s) $(S/B)_l$;
the weight ratio of blocks S2/S1 is from 0.1 to 0.8; preferably 0.1 to 0.6, more preferred 0.15 to 0.40, most preferred 0.15 to 0.3; and
the weight average molecular weight $M_w$ of the block copolymer A is from 220000 to 450000 g/mol, n is a natural number 1 to 8; k, m are 1; and l is a natural number of at least 1, preferably l=1 to 10, more preferably l=1, 2 or 3, most preferably l=1.

A star-shaped structure in terms of the present invention is a structure comprising 1 to 8, preferably 2 to 5, more preferably 3 to 5, most preferred 3 to 4, branches with the same sequences coupled via a linking agent, wherein each branch has the structure of a block copolymer as described above. In the structure (I) above, n is preferably 2 to 5, more preferably 3 to 5, most preferred 3 or 4.

Further, a star-shaped structure block copolymer in terms of the present invention is a block copolymer which is obtained by forming branches of the copolymer by sequential polymerization and after that coupling the branches by addition of a suitable coupling agent, e.g. by a polyfunctional (di- or multi-functional) coupling agent. Suitable coupling agents are known to those skilled in the art and described later. The process for preparation of the inventive block copolymers is described below. As a skilled person knows it will be possible that some of the active polymer chains become terminated rather than reacting with the coupling agent.

In terms of the present invention, the block copolymer having star-shaped structure may also be a product mixture comprising star shaped structure polymers and terminated single chains.

Preferably, the proportion of the blocks $S_1$ and $S_2$—based on the entire block copolymer A—is 25 to 39 wt.-%, more preferred 26 to 35 wt.-%, in particular 26 to 33 wt.-%;

Preferably, the weight average molecular weight $M_w$ of the block copolymer A is from 250000 to 420000 g/mol, more preferably 260000 to 400000 g/mol.

The melt flow index (MFI) of block copolymer A according to the invention preferably is below 3.5 cm³/10 min (200° C. and 5 kg).

More preferably, the vinylaromatic monomer/diene (=S/B) ratio of all of the blocks (S/B) is from 0.5 to 1.0, more preferably from 0.55 to 0.95.

Preferably, the vinylaromatic monomer/diene (=S/B) ratio of the copolymer block $(S/B)_k$ is from 0.5 to 1.0, more preferably from 0.65 to 0.85.

Preferably, the vinylaromatic monomer/diene (=S/B) ratio of the copolymer block(s) (S/B)$_l$ is from 0.5 to 1.2, more preferably from 0.7 to 1.1.

The soft block $(S/B)_l$ may have been subdivided into two or more random soft blocks with different molecular weights and/or different monomer compositions within the aforementioned ranges.

Preferably, the vinylaromatic monomer/diene (=S/B) ratio of the copolymer block $(S/B)_m$ is from 0.3 to 0.8, more preferably from 0.40 to 0.70.

Preferably, the weight average molar mass $M_w$ (determined by GPC according to ISO 16014-3:2012) of the blocks $(S/B)_k$, $(S/B)_l$ and $(S/B)_m$ is different from each other. More preferably $M_w$ of block $(S/B)_l$ is higher than $M_w$ of block $(S/B)_k$ and $M_w$ of block $(S/B)_k$ is higher than $M_w$ of block $(S/B)_m$.

Preferably, the weight-average molecular weight Mw of the copolymer block $(S/B)_k$ is in the range of from 16500 to 40000 g/mol, more preferably 18500 to 31200 g/mol.

Preferably, the weight-average molecular weight Mw of the copolymer block $(S/B)_l$ is in the range of from 25800 to 60800 g/mol, more preferably from 28800 to 48000 g/mol.

Preferably, the weight-average molecular weight Mw of the copolymer block $(S/B)_m$ is in the range of from 14300 to 33800 g/mol, more preferably from 16000 to 26700 g/mol.

Preferably, the weight-average molecular weight Mw of the polymer block $S_1$ is in the range of from 22900 to 54000 g/mol, more preferably from 25600 to 42660 g/mol. Preferably, the weight-average molecular weight Mw of the polymer block $S_2$ is in the range of from 5000 to 12000 g/mol, more preferably from 5700 to 9500 g/mol.

The vinylaromatic monomer is preferably chosen from styrene, α-methylstyrene and/or vinyltoluene, in particular styrene. The diene is preferably chosen from isoprene and/or butadiene. Particular preference is given to butadiene.

The random copolymer blocks S/B are preferably made from one vinylaromatic monomer and one diene, in particular from styrene and butadiene.

The coupling center X is formed by reaction of the living anionic polymer chain ends (=linked by way of the blocks $S_2$ with a polyfunctional coupling agent. Said coupling agent can generally be any suitable polyfunctional compound. It is preferably selected from epoxidized vegetable oils, in particular epoxidized linseed oil or epoxidized soybean oil.

The copolymer blocks B/S composed of polymerized vinylaromatic monomers and of dienes have a random distribution. These can by way of example be obtained by anionic polymerization using alkyllithium compounds in the presence of randomizers, such as tetrahydrofuran, or potassium salts.

Preference is given to use of potassium salts where the molar ratio of anionic initiator to potassium salt is in the range from 25:1 to 60:1, particularly preferably from 30:1 to 40:1. This method can at the same time achieve a low proportion of 1,2 linkages of the butadiene units. Suitable potassium salts are particularly potassium alcoholates, in particular those soluble in the polymerization solvent, e.g. tertiary alcoholates having at least five carbon atoms such as tert-amyl alcoholate or triethylcarbinolate, or other C-rich tertiary alcoholates.

The proportion of 1,2 linkages of the butadiene units is preferably in the range from 8 to 15%, based on the entirety of the 1,2, 1,4-cis, and 1,4-trans linkages.

In the case of polymers prepared anionically, the molecular weight is controlled by way of the ratio of amount of monomer to amount of initiator. The molecular weights are usually determined by means of gel permeation chromatography (GPC) in THF as solvent, using polystyrene as standard.

The star shaped block copolymers A of the invention are produced via anionic polymerization generally in a nonpolar solvent, where the initiation process uses an initiator which is generally an organometallic compound. The production process in the invention uses addition of at least one coupling agent, generally at the end of the polymerization reaction, where the at least one initiator is added at the start of the polymerization reaction.

The process of the invention permits production of the block copolymers A of the invention which in particular feature star-shaped molecular architecture with identical arms (branches) of the star.

Suitable initiators in the anionic polymerization reaction are organometallic compounds, preferably compounds of the alkali metals, particularly preferably of lithium. Examples of initiators are methyllithium, ethyllithium, propyllithium, n-butyllithium, sec-butyllithium, and tert-butyllithium. The organometallic compound is generally added in the form of solution in a chemically inert hydrocarbon. The amount added depends in principle on the desired molar mass of the polymer, but is generally from 0.002 to 5 mol %, based on the monomers. Solvents used are preferably aliphatic hydrocarbons, such as cyclohexane or methylcyclohexane.

The anionic polymerization reaction also generally uses addition of a polar cosolvent (as randomizer), and it is believed here that the cosolvent acts as Lewis base in relation to the metal cation of the initiator.

Preferred Lewis bases are polar aprotic compounds such as ethers and tertiary amines. Examples of particularly effective ethers are tetrahydrofuran and aliphatic polyethers, such as ethylene glycol dimethyl ether and diethylene glycol dimethyl ether. Tertiary amines that may be mentioned are triethylamine, tributylamine, and pyridine. The amount of the polar co-solvent added to the nonpolar solvent is by way of example from 0.5 to 5% by volume. Particular preference is given to an amount of from 0.1 to 0.6% by volume of tetrahydrofuran. An amount of from 0.2 to 0.4% by volume is very particularly preferred in many instances.

The amount added of, and the structure of, the Lewis base determine the copolymerization parameters and the proportion of 1,2- and 1,4-linkages of the diene units. The resultant block copolymers generally have a proportion of from 20 to 80% of 1,2-linkages and from 80 to 20% of 1,4-linkages, based on all of the diene units.

Preferably, a soluble potassium salt is added (as randomizer)—instead of the cosolvent—and is in particular a potassium alcoholate. It is believed here that the potassium salt interacts by metal exchange with the lithium-carbanion ion pair, thus forming potassium-carbanion compounds which preferentially form adducts with the vinylaromatic monomer, preferably styrene, whereas the lithium-carbanion compounds preferentially form adducts with the diene, particularly preferably butadiene. Since potassium-carbanion compounds are substantially more reactive, even a small fraction, namely from 1/10 to 1/50, is sufficient, together with the predominating lithium-carbanion compounds to give a similar average probability of incorporation of vinylaromatic monomers, preferably styrene, and of dienes, particularly preferably butadiene. Preference is given to use of potassium salts where the molar ratio of anionic initiator to potassium salt is in the range from 25:1 to 60:1, preferably from 30:1 to 40:1. Particularly preferably selected is a molar lithium/potassium ratio of from 33 to 39 in order to achieve approximately identical incorporation of vinylaromatic monomer, preferably styrene, and diene, preferably butadiene.

It is moreover believed that during the polymerization procedure there is frequent metal exchange between the living chains and also between a living chain and the dissolved salt, and that the same chain forms an adduct on one occasion preferentially with a vinylaromatic monomer, preferably styrene, and in turn on another occasion with a diene, particularly preferably butadiene. The resultant copolymerization parameters are then approximately the same for the vinylaromatic monomer and the diene. Suitable potassium salts are particularly potassium alcoholates, in particular those soluble in the polymerization solvent, e.g. tertiary alcoholates having at least five carbon atoms such as tert-amyl alcoholate or triethylcarbinolate, or other C-rich tertiary alcoholates.

Examples of typical corresponding alcohols are 3-ethyl-3-pentanol and 2,3-dimethyl-3-pentanol. Tetrahydrolinalool (3,7-dimethyl-3-octanol) and 2-methyl-2-butanol (tert-amylalcohol) prove to be particularly suitable. Other compounds also suitable in principle alongside the potassium alcoholates are other potassium salts which are inert toward alkyl metal compounds. Mention may be made of dialkylpotassium amides, alkylated diarylpotassium amides, alkyl thiolates, and alkylated aryl thiolates.

The polymerization temperature is generally from 0 to 100° C., preferably from 30 to 90° C., particularly preferably from 45 to 90°. The polymerization reaction is generally carried out in a plurality of stages, where the initiator is added at the start of the polymerization using a single initiation process. By way of example, the process begins by producing the hard block $S_1$. A portion of the monomers is used as initial charge in the reactor, and the polymerization reaction is initiated via addition of the initiator. In order to achieve a defined chain structure that can be calculated from the amount of monomer and of initiator added, it is advisable to achieve high conversion (above 99%) in the process before the second monomer addition takes place. However, this is not essential.

The sequence of monomer addition depends on the selected block structure. In the case of a batch process, it is preferable to begin by using all of, or a portion of, the solvent, such as cyclohexane, as initial charge, and then to use, as initial charge, the amount of initiator, such as sec-butyllithium, that is required to establish the desired molar mass, plus what is known as a titration amount, which serves to destroy traces of impurities in the solvent and in the tank. It is then preferable to add the potassium salt, such as potassium tert-amyl alcoholate, preferably dissolved in cyclohexane, or to add the complexing solvent, such as THF to the reactor, and then to add the first amount of vinylaromatic monomer, in order to produce the block $S_1$. Diene and vinylaromatic monomer for the preparation of block $(S/B)_k$ are then added, preferably simultaneously.

The addition can take place in a plurality of portions optionally together with further solvent, e.g. for improved heat dissipation, and as a function of the desired constitution. The random structure, and the constitution, of the blocks S/B are determined via the quantitative proportion of diene with respect to vinylaromatic compound, the concentration of the potassium salt, if a potassium salt is used, and the concentration and chemical structure of the Lewis base used as co-solvent, if a Lewis base is used, and also the temperature.

Then the block $(S/B)_l$ is (or sub blocks $(S/B)_{l1}$, $(S/B)_{l2}$ etc. can be) polymerized onto the growing polymer chain via addition of diene and vinylaromatic monomers. Preferably only one block $(S/B)_l$ is then polymerized onto the growing polymer chain. Then the addition of the diene and vinylaromatic monomers used for polymerizing the block $(S/B)_m$ onto the growing polymer chain takes place. At last vinylaromatic monomer is added in order to produce the block $S_2$.

According to the process of the invention, coupling with a coupling agent takes place after the last addition of vinylaromatic monomer, and the plurality of polymer blocks $S_2$ are thus bonded to one another, and the block copolymer A of the invention having star-shaped molecular architecture is formed.

It is generally possible to use any polyfunctional (di- or multifunctional) compound as coupling agent. It is preferable that the coupling agent has been selected from epoxidized vegetable oils, such as epoxidized linseed oil or epoxidized soybean oil, silanes, such as alkoxysilanes, e.g. $Si(OMe)_4$, chlorosilanes, such as $SiCl_4$, $Si(alkyl)Cl_3$, where alkyl is a $C_1$-$C_4$-alkyl moiety, preferably methyl, halides of aliphatic hydrocarbons, such as tin tetrachloride; preferred coupling agents are epoxidized vegetable oils, such as epoxidized linseed oil or epoxidized soybean oil.

The coupling agent forms the coupling center X, which is formed by reaction of the living anionic chain ends with one of the abovementioned coupling agents.

The amount of coupling agent is calculated as a function of its functionality and of the amount of initiator used. It is preferable to add the amount of coupling agent needed for reacting all of the living chains, corresponding to the amount of active initiator (total amount of initiator minus titration amount). In the case of ester groups, account has to be taken of the fact that these form two living chains, whereas in contrast epoxides and haloalkanes and -silanes form one per functional group. By way of example, epoxidized soybean oil comprises fatty acids esterified in the form of triglyceride having predominantly one or two epoxy groups, and correspondingly predominantly forms bonds with three or four polymer chains, liberating the metal alcoholate of glycerol, since the carboxy group also forms bonds with two further chains.

In the case epoxidized vegetable oils, such as epoxidized linseed oil or epoxidized soybean oil, are used as coupling agent, only approximately 70% of all living polymer chains are coupled to the coupling agent. The remaining 30% of the living polymer chains become terminated rather than reacting with the coupling agent and remain uncoupled in the polymer matrix of star shaped block copolymer A.

The polymer concentration can be varied widely, but should preferably be selected in such a way that the temperatures at the end of the polymerization reaction for the individual blocks do not exceed values of 100° C. or if they exceed that value then at most for a short time, thus avoiding any significant premature thermal termination.

Typical polymer concentrations after the coupling process, in the case of a batch process in a stirred tank, are from 10 to 50% by weight, preferably from 12 to 40% by weight, and particularly preferably from 15 to 35% by weight.

Instead of a stirred tank, preferably in combination with a reflux condenser, where the internal pressure of the tank is preferably lowered to cool the reaction solution via boiling and reflux of the solvent, it is in principle also possible to use other types of reactor, for example a loop reactor in combination with a cooled section, such as a heat exchanger, or to use a stirred tank in combination with an external heat exchanger. Instead of producing the block copolymers A of the invention in a batch process, they can be produced in a continuous process via, for example, arrangement in series of the reactors listed above in various combinations, or in a tubular reactor with preferably static mixing elements, or via a combination of tubular reactor and the reactors listed above. The number of reaction zones is preferably the same as the number of different monomer additions plus the coupling agent addition.

At the start, and at the appropriate points, the initiator system, generally comprising initiator and randomizer and optionally further solvent, is additionally mixed; it is preferable here to add the solvent to the monomer feeds so that the monomer is in dilute form before it reaches the reactor.

In one preferred embodiment, the polymer concentration is kept constant in the range from 15 to 35% by weight along the reactor cascade. In another preferred embodiment, the polymer concentration is increased to from 36 to 50% by weight through the final monomer addition.

Thus, the process according to the invention for the preparation of block copolymer A is characterized by the following features:
 i) a single initiation,
 ii) first addition and polymerization of vinyl aromatic monomer,
 iii) at least 3 times addition and polymerization of a vinyl aromatic monomer and diene mixture,
 iv) second addition and polymerization of vinyl aromatic monomer, and
 v) a coupling step after the addition and polymerization of the vinylaromatic monomers of the last polymer block.

The further work-up of the elastomeric block copolymer of the invention takes place by conventional processes. It is advisable here to operate in a stirred tank and, after the coupling process, optionally use a small amount of alcohol, such as isopropanol, to protonate the possible small amounts of residual carbanions and the polymer-bonded alcoholates which may have been produced in the coupling step, in order to avoid formation of deposits in the tank and discoloration of the product, and to lower the viscosity of the solution, and, prior to further work-up, to use $CO_2$/water in a conventional manner to acidify the product slightly, so that the product subsequently obtained is glass-clear with no color tinge.

It is also useful to stabilize the polymer with a free-radical scavenger or preferably with a combination of free-radical scavengers (e.g. C-free-radical scavengers, such as α-tocopherol (vitamin E), Sumilizer® GM and Sumilizer® GS, in combination with O-free-radical scavengers, such as Irganox® 565, Irganox® 1010 and Irganox® 1076) and with a secondary oxidation inhibitor (e.g. commercially available products preferably based on phosphite, an example being triisononylphenyl phosphite (TNPP) or Irgafos® 168), and use the conventional processes to remove the solvent, and extrude and pelletize the product.

One preferred process for removing the solvent is to decrease the concentration of the solvent in stages, where, if the polymerization reaction uses a batch process, the solution is advantageously first placed into intermediate storage in a buffer tank, and then is preferably after passage through a pump heated by way of one or more heat exchangers in series to a temperature which is preferably from 100 to 140° C. above the boiling point of the solvent (this being from 180 to 220° C. in the case of cyclohexane), in order then after passage through a pressure-retention valve to be transferred via a short pipe with vapor velocities which are preferably from 100 to 350 m/s into a depressurization vessel of which the pressure and temperature are preferably adjusted in such a way that the solvent just begins to condense and the surface has a coating of a solvent film, i.e. is not dry; for cyclohexane as solvent, it is preferable here to select temperatures of from 100 to 140° C. and pressures of from 1.6 to 4.3 bar.

The solvent vapor is preferably discharged upward out of the depressurization vessel, and condensed passed for work-up, while the polymer solution, the concentration of which is now about 70-95%, gives a precipitate in the form of flakes on the base of the vessel, from where it can be conveyed onward by way of example by a gear pump into the next heat exchanger and can be reheated, preferably to from 170 to 230° C.

The solution is then again depressurized by way of a pressure-retention valve onto the screws of a preferably twin-screw extruder, where the solvent vapor is discharged by way of vent domes upstream of and downstream of the polymer feed point.

The concentration of the solvent is then preferably further reduced in extruder segments with barrier screw elements which seal against one another, while the vacuum continues to improve and upstream of the extruder head is preferably from 1 to 300 mbar, and small amounts of water are preferably injected, until the solvent content achieved is preferably <3000 ppm, particularly preferably <2000 ppm.

At the end of the extruder, the melt can be either strand-pelletized or underwater-pelletized, preference being given here to the underwater pelletization process. However, it is also possible to remove the solvent by way of other processes, for example by way of what is known as a Filmtruder in combination optionally with an extruder, or via steam stripping, as is conventional in the case of most styrene-based thermoplastic elastomers. In this case, polymer flakes are obtained. The pellets or the flakes can, like other types of rubber, be protected from adhesion by using an antiblocking agent, such as Acrawax®, Besquare®, Aerosil®, and/or tricalcium phosphate. Also dispersed oils and surfactants as processing aids, like Würtz PAT 906/EMC, in the water-circuit of the underwater granulation can help to reduce the stickiness of the granulate in the water cycle and silo.

A particular feature of the process of the invention is that the block copolymer A of the invention can be produced with good space-time yields. The space-time yield (STY) for a batch polymerization process, i.e. from the juncture at which the first monomer charge has been combined with the initiator charge until conclusion of the coupling process, i.e. the juncture at which optional addition of alcohol and evacuation of the reactor can be started, is generally from 0.5 to 3.5 h, preferably from 1 to 3 h.

Block copolymers A according to the invention are thermoplastic elastomers which are non-sticky and transparent.

Thermoplastic elastomer compositions according to the invention comprising block copolymers A can preferably be used for medical applications e.g. for tubes and soft-touch skin-contact applications.

Component b)

The plasticizer B used in the composition according to the invention is
 b1) a mixture composed of mineral oil B1 and at least one cyclohexane 1,2-dicarboxylic acid $C_8$ to $C_{10}$ dialkyl ester B2; or
 b2) a mixture composed of mineral oil B1 and at least one vegetable oil B3.

Suitable mineral oils B1 (=component B1) are such as low-aromatic paraffinic oils, naphthenic oils or oligomeric polybutadienes. Said paraffinic oils or naphthenic oils include, in particular, white oils which have been purified to medical grade and which have medical approval or approval under food law. Preference is given to white oils as component B1 in particular such having a viscosity of 50 to 100 centistokes (at room temperature).

Suitable as plasticizer component B2 are cyclohexane 1,2-dicarboxylic acid $C_8$ to $C_{10}$ dialkyl esters B2 preferred examples being: di-(2-ethylhexyl) cyclohexane-1,2-dicarboxylate, diisooctyl cyclohexane-1,2-dicarboxylate, diisononyl cyclohexane-1,2-dicarboxylate, di-(2-propylheptyl) cyclohexane-1,2-dicarboxylate or diisodecyl cyclohexane-1,2-dicarboxylate.

It is also possible to use as component B2 mixtures of said cyclohexane-1,2-dicarboxylic acid di-$C_8$ to $C_{10}$ dialkyl esters, or mixed cyclohexane-1,2-dicarboxylic esters prepared from mixtures of $C_8$ to $C_{10}$ alcohols.

It is preferred to use diisononyl cyclohexane-1,2-dicarboxylic esters as component B2, an example being the commercially available product Hexamoll® DINCH (CAS No. Europe and Asia: 166412-78-8; CAS No. USA: 474919-59-0; from BASF SE).

In plasticizer mixture b1) the weight ratio of component B1 to component B2 is preferably 80:20 to 40:60.

According to one preferred embodiment—in particular for applications where a moderate softness is needed—in plasticizer mixture b1) the weight ratio of component B1 to component B2 is 80:20 to 60:40.

According to a further preferred embodiment—in particular for applications where a high softness is needed—in plasticizer mixture b1) the weight ratio of component B1 to component B2 is 60:40 to 40:60.

The cyclohexane 1,2-dicarboxylic acid C8 to C10 dialkyl esters B2 may be prepared in an economically advantageous manner by hydrogenation of the aromatic ring of the corresponding phthalic esters.

Available to the skilled person for this purpose is a series of processes and catalysts examples being the ring hydrogenation process of WO 99/032427, comprising the ring hydrogenation of phthalates at 50 to 250° C. under a pressure of 20 to 300 bar, using transition metal catalysts. Advantageous processes are disclosed in WO 2012/084914 (p. 13, I. 4 to 14, I. 18) which is expressly incorporated by reference.

Suitable vegetable oils B3 (=component B3) having a iodine value (g/100 g) of no more than 130 are for example vegetable oils selected from the group consisting of: rapeseed oil, sunflower oil, grape seed oil, palm oil, olive oil, coconut oil, palm kernel oil, cocoa butter, jojoba oil, cottonseed oil, corn oil, wheat germ oil, soybean oil, peanut oil, castor oil, sesame oil and rice brain oil. Preferred as component B3 is rapeseed oil (also known as canola oil). It is also possible to use as component B3 a mixture of said vegetable oils B3. Preferably only one vegetable oil B3 is used.

In plasticizer mixture b2) the weight ratio of component B1 to component B3 is preferably 80:20 to 40:60.

According to one preferred embodiment—in particular for applications where a moderate softness is needed—in plasticizer mixture b1) the weight ratio of component B1 to component B3 is 80:20 to 60:40.

According to a further preferred embodiment—in particular for applications where a high softness is needed—in plasticizer mixture b1) the weight ratio of component B1 to component B3 is 60:40 to 40:60.

Vegetable oils B3 can be used as naturally occurring but preferably the vegetable oils B3 are purified prior to use by deodorization and removal of the free fatty acids and phosphatides and other easy oxidizing moieties.

Preferred as plasticer B is plasticizer mixture b2). In particular preferred is the use of plasticizer mixture b2) wherein component B3 is rapeseed oil.

Component c)

The further additives C which can be optionally present as component c) in the thermoplastic elastomer composition according to the invention do not include plasticizers. Additives C are in particular selected from stabilizers, antiblocking agents, dyes, flame retardants and UV absorbers.

Preferred is the use of a stabilizer, in particular oxygen radical scavengers such as Irganox® 1010 (BASF SE), Songnox® 1010, Irganox 1076, Irganox 565 and blends thereof, carbon radical scavengers such as Zikanox®, Sumilizer® GS, Sumilizer GM and blends thereof, and/or secondary stabilizers such as Irgafos® 168. Said stabilizers are commercially available. The afore-mentioned stabilizers are preferably used in amounts of 0.01 to 0.5 wt.-%, more preferably 0.02 to 0.3 wt.-%.

Further preferred is the use of antiblocking agents, such as Acrawax® (Lonza), Besquare®, Aerosil®, and/or tricalcium phosphate. The afore-mentioned stabilizers are preferably used in amounts of 0.005 to 0.5 wt.-%, more preferably 0.01 to 0.3 wt.-%.

Process for the Preparation of Thermoplastic Elastomer Compositions of the Invention The thermoplastic elastomer composition (or molding composition) according to the invention may be obtained by mixing and homogenizing the components a), b) and, if present, c) by the usual methods of plastics technology, and the sequence of adding the components may be varied. Examples of suitable mixing equipment are continuous or batch kneaders, Banbury mixers, or co-rotating or counter rotating single- or twin-screw extruders.

Preferably block copolymers A are introduced continuously into an extruder and then plasticizer B and optionally further components c) are metered in.

A further preferred variant of incorporating component b) and optional components c) into component a) is to meter component b) and optional component c) (can be used as such or in solution) into the polymer solution (e.g. in cyclohexane) of block copolymer A in the form in which it is present, for example, after the polymerization, then to homogenize the liquids, if desired, using a stirrer in a vessel or a static mixer or a combination of both, and subsequently to free the product from the solvent. This preferred so-called impregnation variant can either be by addition of components a), b), and c) in a continuously stirred vessel or by adding the components b) and c) to a processing pipe with the solution of component a) and mixing by use of a static mixer. Components b) and c) can be added at the same time or at different stages in the process or in time (i.e. after each other in a vessel, in successive vessels, with static mixer between each addition, etc) and in all orders. Preferably, in case stabilizer additives C are used as component c), said stabilizer additives C are added before component b).

Preferably, an impregnation with static mixer is used in which the stabilizer additives C are added first, followed by a static mixer, followed by the addition of component b) and finally followed by the last static mixer. Afterwards, the mixture is degassed as described for working-up below.

Depending on whether the block copolymer A has been produced in the form of flakes (as for example by steam stripping of the organic polymerization solvent), in the form of compacts, through compression of the aforementioned flakes, or in the form of pellets, by prior extrusion, different production processes for the mixtures are preferred. Flakes and compacts are preferably mixed first with the plasticizer B preferably in an apparatus which subjects the flakes to little or no shearing. This may be a rotating drum, a paddle mixer or a slow-running compounder. Suitable compounders/mixers are described in, for example, Kunststoff-Handbuch, Hanser Verlag, Munich, 1975, in Section 5.1.2.1, pages 965 to 975.

Depending on the surface nature of the flakes or of the compacts, the plasticizer B migrates into the polymer at a different rate, with a larger surface-volume ratio accelerating the incorporation. Mixing is carried out preferably until all of the oil is bound. The contact time may amount to 1 minute to 1 day, preferably 2 minutes to one hour. The temperature is preferably between 20 and 200° C., preferably between 25 and 100° C., more preferably between 30 and 50° C. The polymer/oil mixture is then transferred preferably to a single-screw or twin-screw or multiscrew compounder or extruder (for example, a ZSK from Coperion, formerly Werner & Pfleiderer), a BUSS kneader (Buss AG, Pratteln, Switzerland) or a LIST reactor (List AG, Arisdorf, Switzerland), and the temperature therein is raised by external heating and/or shearing to temperatures of more than 100° C., preferably more than 140° C. Suitable compounders/extruders are described in, for example, Kunststoff-Handbuch, Hanser Verlag, Munich, 1975, in Section 5.1.3.3, pages 1029 to 1091. The compounder may be fed at various points with further additives C.

If additives C are stabilizers, they need to be dosed in the above-described impregnation step (polymer solution).

The plasticizer B as component b) can be added at a stage as hereinbefore described but also earlier during production of component a) by impregnation or by feed in a stirred vessel or in the reactor after the termination of the polymerization. Where the block copolymer A is in the form of pellets with a sufficient melt flow rate, it may be melted alone in an extruder and the plasticizer B may be metered in at a later point. Likewise preferred is the simultaneous metering of plasticizer B and pellets and of any further additives C (except from stabilizers).

The ready-homogenized mixture may then be worked up preferably by underwater pelletizing (hot chopping) or strand pelletizing (cold chopping), or the melt may be processed further in an injection molding machine.

Examples of further suitable continuous or discontinuous mixing elements include roll mills, Branbury kneaders, and similar elements.

Working up is accomplished preferably via multistage devolatilization with flash evaporation in the first step, the solution, prior to the evaporation, being heated in a heat exchanger to 150 to 250° C., preferably to 180 to 220° C., under superatmospheric pressure, and let down through a throttle valve preferably against pressures of between 100 mbar and 5 bar, more preferably 500 mbar to 2 bar, with the solvent, preferably cyclohexane or other hydrocarbons suitable, for example, for the anionic polymerization for preparing the block copolymers A, being very largely evaporated, preferably down to a residual amount of 1 to 20%.

The melt is preferably heated again to temperatures between 150 and 250° C. and let down again, via a pressure-maintenance valve, into a conveying element, preferably a single-screw or twin-screw or multiscrew extruder, preferably against pressures of between 500 mbar and 2 bar. The pressure can be reduced in a plurality of stages via the devolatilization domes of the extruder, down to preferably 1 to 500 mbar, preferably 5 to 400 mbar, with the temperature of the polymer melt being held preferably at between 120 and 280° C., preferably between 160 and 240° C. The melt may then be converted into pellet form by means, for example, of underwater pelletization.

Arranged at the end of the extruder, preferably, is an underwater pelletizer, also called a hot chopper, of the kind available, for example, from Gala. The residence time of the water/pellets mixture is preferably 10 seconds to 60 minutes, more preferably 2 to 15 minutes, in order to lessen the tendency of the pellets to stick. The water/pellets mixture is then separated preferably via a sieve, with the water being preferably circulated and cooled via a heat exchanger. The water preferably comprises an antiblocking agent in order to prevent the individual pellets from sticking to one another, preferably a fatty acid amide dispersion. The sieved pellets are subsequently blown dry preferably in a stream of air, and are dusted preferably with a further antiblocking agent in powder form, such as tricalcium phosphate or silica, for example. It can then be moved to a silo or packaged into sacks or other packaging means.

The thermoplastic elastomer compositions of the invention are non-sticky, very soft, thermoplastically processable, and readily recyclable by remelting.

Owing to the outstanding processing properties and compatibility with styrene-based thermoplastics, such as glass-clear polystyrene (GPPS), high-impact polystyrene (HIPS), styrene-butadiene block copolymers such as Styrolux® from Ineos Styrolution or K-Resin® (Ineos Styrolution), styrene-acrylonitrile polymers (SAN), acrylonitrile-butadiene-styrene polymers (ABS) or polyphenylene ethers (PPE) or GPPS/PPE mixtures, the thermoplastic elastomer compositions of the invention are appropriate for two-component {2C} injection molding or they can be easily joint just by solvent gluing.

The boundary between the afore-mentioned hard components and the thermoplastic elastomer compositions of the invention as soft components is transparent, moreover. With 2C injection molding, it is thus possible to produce flexible and rigid parts in one molding procedure. Also suitable as a hard component are polyesters such as polybutylene terephthalate, but also those with other diol components such as 1,3-propanediol, those with adipic acid, sebacic acid, succinic acid, and other aliphatic dibasic acids, including in combination with aromatic dicarboxylic acids, polycarbonate or mixtures thereof, preferably on the basis of bisphenol A.

The thermoplastic elastomer compositions according to the invention are suitable for many applications.

A further subject of the invention is the use of the thermoplastic elastomer compositions according to the invention for producing elastic and flexible moldings and shaped articles, preferably medical articles, in particular medical articles for skin contact applications such as braces and diapers and intravenous applications like bags and tubings.

Shaped articles produced from the transparent thermoplastic elastomer compositions of the invention are very soft and have good mechanical properties (e.g. E-modulus, stress at break and strain at break).

The examples below and the patent claims illustrate the invention.

EXAMPLES

Plasticizer B:
B1 Winog® 70, a commercially available medical white oil
B2 Hexamoll® (DINCH) from BASF SE, Germany
B3 Rapeseed oil, Agri-pure® AP-60 from Cargill
Block Copolymer A1

A star-shaped block copolymer A of the structure $[S_1—(S/B)_k—(S/B)_l—(S/B)_m—S_2]_n—X$ was prepared by sequential anionic polymerization of styrene (monomers S1 to S5) and butadiene (monomers B1 to B3) (cp. Table 1), and subsequent coupling using epoxidized soybean oil. 25670 ml of cyclohexane were used as initial charge (ic) and titrated to the end point at 45° C. with 1.6 ml of sec-butyllithium (BuLi ic), and cooled to 45° C. before adding the volume of a 1.4 M sec-butyllithium initiator solution as mentioned in Table 2, (BuLi) for initiation, and the volume of a 0.3304 M potassium tert-amyl alcoholate (PTA) randomizer solution as mentioned in Table 2. Next, the initiator mixture was then admixed and the mixture was cooled to 40° C. In a next step, 1350 gram styrene (S1) was added and the polymerization reaction was allowed to run to complete monomer consumption (identified by a decrease in temperature of the reaction mixture). In a next step, 570 gram butadiene (B1) and 415 gram styrene (S2) were added simultaneously and the polymerization reaction was allowed to run to complete monomer consumption (identified by a decrease in temperature of the reaction mixture).

In a next step, again 800 gram butadiene (B2) and 720 gram styrene (S3) were added simultaneously and the polymerization reaction was allowed to run to complete monomer consumption (identified by a decrease in temperature of the reaction mixture). In a next step, again 535 gram butadiene (B3) and 310 gram styrene (S4) were added simultaneously and the polymerization reaction was allowed to run to complete monomer consumption (identified by a decrease in temperature of the reaction mixture). In a next step, 300 gram styrene (S5) was added and the polymerization reaction was allowed to run to complete monomer consumption (identified by a decrease in temperature of the reaction mixture).

Finally, the amount of Edenol® D82 as mentioned in Table 2, dissolved in 10 mL cyclohexane, was added at a temperature between 45 and 55° C. as coupling agent and allowed to react for 10 minutes. Finally, 5 ml of isopropanol was added and the mixture was stirred during 10 min. Next, the mixture was acidified with 10 mL destilled water and 5 min of $CO_2$ gas stream (0.1 kg/h) while stirring. Finally, 0.135 wt.-% phm*Irganox 1010, 0.180 wt.-% phm*Irgaphos 168 and 0.135 wt.-% phm*Sumilizer GS were added.

*phm='per hundred parts by weight of monomer' (wt.-% of component (initiator, coupling agent etc.) is calculated on the total mass of the monomers).

TABLE 1

Block copolymer A (composition and sequence of addition)

| 1st block $S_1$ | 2nd block $(S/B)_k$ | | 3rd block $(S/B)_l$ | | 4th block $(S/B)_m$ | | 5th block $S_2$ |
|---|---|---|---|---|---|---|---|
| S1 wt.-% | B1 wt.-% | S2 wt.-% | B2 wt.-% | S3 wt.-% | B3 wt.-% | S4 wt.-% | S5 wt.-% |
| 27.0 | 11.4 | 8.3 | 16.0 | 14.4 | 10.7 | 6.2 | 6.0 |

Block copolymers A1 to A8 of different weight average molar masses $M_w$ were obtained in accordance with the preparation as hereinbefore described (cp. Table 1) by use of the appropriate amount of BuLi, PTA and Edenol (cp. Table 2).

Table 2 shows further the determined Shore A hardness of S-TPE compositions comprising one of the block copolymers A1 to A8 and different amounts of plasticizer B (mixture of B1/B2 or B1/B3 used in highest B1/B2 or B1/B3-ratio in which no bleeding occurs, cp. Table 4).

TABLE 2

| Polymer | BuLi 1.4M mL | PTA randomizer mL | Edenol mL | $M_{peak}$ before coupling g/mol | $M_w$ after coupling g/mol | Plasticizer B* phm | Shore A ASTM D2240 (15 sec) |
|---|---|---|---|---|---|---|---|
| A1 | 42.26 | 5.12 | 6.53 | 100240 | 252950 | 10 | 70 |
| A2 | 37.72 | 4.57 | 5.83 | 112310 | 296540 | 15 | 64 |
| A3 | 34.68 | 4.20 | 5.36 | 122150 | 290270 | 20 | 58 |
| A4 | 33.01 | 4.00 | 5.10 | 128310 | 318020 | 25 | 50 |
| A5 | 31.20 | 3.78 | 4.82 | 135770 | 352430 | 30 | 45 |
| A6 | 28.46 | 3.45 | 4.40 | 148820 | 390720 | 35 | 43 |
| A7 | 28.45 | 3.44 | 4.40 | 148870 | 367850 | 40 | 40 |
| A8 | 26.78 | 3.24 | 4.14 | 158190 | 403480 | 45 | 38 |

Block Copolymer C1 (Comparative Compound)

Linear block copolymer C1 of the structure $S_1$—$(B_1/S_2)$—$(B_2/S_3)$—$(B_3/S_4)$—$S_5$ (cp. Table 3) was prepared by sequential anionic polymerization of styrene (monomers S1 to S5) and butadiene (monomers B1 to B3), and subsequent terminating using 15 mL isopropanol. Linear block copolymer C1 was prepared in a manner similar to that as described for block copolymer A above, except of the coupling step, and further that 17970 mL cyclohexane was used as a solvent, in each case 960 g of styrene were used for the terminal blocks S, a mixture of 660 g of styrene and 700 g of butadiene for the random soft block ($B_1/S_2$), a mixture of 852 g of styrene and 904 g of butadiene for the random soft block ($B_2/S_3$) and a mixture of 468 g of styrene and 496 g of butadiene for the random soft block ($B_3/S_4$). The polymerisation was initiated using 37.59 mL of a 1.4 M sec-butyllithium solution and 4.49 mL of a 0.304 M potassium tert-amyl alcoholate (PTA) solution. After termination of the polymerization, the mixture was acidified with 10 mL destilled water and 5 min of $CO_2$ gas stream (0.1 kg/h) while stirring. Finally, 12 gram Irganox 1010, 16.2 gram Irgaphos 168 and 12 gram Sumilizer GS were added.

Mw: 141930 g/mol

Shore A (ASTM D2240 (15 sec)): 84

TABLE 3

Block copolymer C (composition and sequence of addition)

| SBC | Ini 1 BuLi1 (1.4M) wt.-% (phm*) | 1st block $S_1$ S1 wt.-% | 2nd block $(B_1/S_2)$ | | 3rd block $(B_2/S_3)$ | | 4th block $(B_3/S_4)$ | | 5th block $S_2$ |
|---|---|---|---|---|---|---|---|---|---|
| | | | B1 wt.-% | S2 wt.-% | B2 wt.-% | S3 wt.-% | B3 wt.-% | S4 wt.-% | S5 wt.-% |
| C1 | 16.0 | 11.7 | 11.0 | 15.1 | 14.2 | 8.3 | 7.8 | 16.0 | |

Preparation of S-TPE Compositions

In a stirred vessel to a cyclohexane solution (polymer content 27.8 wt.-%) of one of the obtained stabilized block copolymers A1 to A8 or block copolymer C1, 0 to 45 phm of plasticizer B (based on 100 parts by weight (phm) of the total monomer weight used during the synthesis of block-copolymer A) were added and homogeneously mixed at 60° C. Each solution was subsequently degassed and the S-TPE compositions for further testing (cp. Tables 2, 4 and 5) were obtained.

Bleeding Tests

The samples with different plasticizer concentrations and plasticizer compositions (cp. Table 4) were compression molded to plates and cut into pieces (3 cm×3 cm). Next, the samples were stored on absorption paper under a load of 5 kg and at 35° C. After 1 week, the bleeding of the plasticizer B into the absorption paper was assessed according to next scale:

0=No bleeding (=non-sticky)
1=Bleeding stains onto the absorption paper
2=Bleeding stains onto the absorption paper+greasy polymer sample Table 4 shows that the oil-uptake without bleeding can be increased by use of the inventive S-TPE compositions comprising block copolymer A (cp. inventive samples 27 and 28 with a total plasticizer B concentration of 40 phm). Even with a total oil concentration of 45 phm a bleeding score of 0 can be achieved.

TABLE 4

| No. | Plasticizer B** (phm) | Block copolymer C | Block copolymer A | Fraction of B1 (wt.-%) based on B | Fraction of B3 (wt.-%) based on B | Fraction of B2 (wt.-%) based on B | Bleeding score block copolymer C | Bleeding score block copolymer A |
|---|---|---|---|---|---|---|---|---|
| 1 | 10 | C1 | A1 | 100 | | | 1 | 1 |
| 2 | | | | 80 | 20 | | 0 | 0 |
| 3 | | | | 80 | | 20 | 0 | 0 |
| 4 | | | | 60 | 40 | | 0 | 0 |
| 5 | | | | 60 | | 40 | 0 | 0 |
| 6 | | | | 40 | 60 | | 0 | 0 |
| 7 | | | | 40 | | 60 | 0 | 0 |
| 8 | 20 | C1 | A4 | 100 | | | 2 | 2 |
| 9 | | | | 80 | 20 | | 0 | 0 |
| 10 | | | | 80 | | 20 | 2 | 2 |
| 11 | | | | 60 | 40 | | 0 | 0 |
| 12 | | | | 60 | | 40 | 0 | 0 |
| 13 | | | | 40 | 60 | | 0 | 0 |
| 14 | | | | 40 | | 60 | 0 | 0 |
| 15 | 30 | C1 | A5 | 100 | | | 2 | 2 |
| 16 | | | | 80 | 20 | | 2 | 2 |
| 17 | | | | 80 | | 20 | 2 | 2 |
| 18 | | | | 60 | 40 | | 0 | 0 |
| 19 | | | | 60 | | 40 | 0 | 0 |
| 20 | | | | 40 | 60 | | 0 | 0 |
| 21 | | | | 40 | | 60 | 0 | 0 |
| 22 | 40 | C1 | A7 | 100 | | | 2 | 2 |
| 23 | | | | 80 | 20 | | 2 | 2 |
| 24 | | | | 80 | | 20 | 2 | 2 |
| 25 | | | | 60 | 40 | | 2 | 2 |
| 26 | | | | 60 | | 40 | 2 | 2 |
| 27 | | | | 40 | 60 | | 1 | 0 |
| 28 | | | | 40 | | 60 | 1 | 0 |
| 29 | 45 | C1 | A8 | 100 | | | 2 | 2 |
| 30 | | | | 80 | 20 | | 2 | 2 |
| 31 | | | | 80 | | 20 | 2 | 2 |
| 32 | | | | 60 | 40 | | 2 | 2 |
| 33 | | | | 60 | | 40 | 2 | 2 |
| 34 | | | | 40 | 60 | | 2 | 1 |
| 35 | | | | 40 | | 60 | 2 | 0 |

**total plasticizer B concentration (phm) on top of total weight of monomers of block copolymer A or C Mechanical Properties The samples with different plasticizer concentrations and plasticizer compositions were compression molded to plates with 2 mm thickness at 200° C. Next, the tensile test bars, according to ISO 527-1A, were pneumatically pressed from this compression molded plates (>1 cm from the edges) and tempered for 24 hours at 23° C. Finally, the bars were subjected to a tensile test on a Zwick tensile tester (2.5 kN+500N) according to the ISO 527 procedure.

The resulting E-modulus, stress at break and strain at break are given in Table 5 below.

TABLE 5

| Sample | Block copolymer A | Plasticizer B** (phm) | Fraction of B1 (wt.-%) based on B | Fraction of B3 (wt.-%) based on B | Fraction of B2 (wt.-%) based on B | E-modulus (MPa) | Stress at break (MPa) | Strain at break (%) |
|---|---|---|---|---|---|---|---|---|
| A | A3 | 15 | 80 | | 20 | 4.7 | 12.4 | 881 |
| B | | | 80 | 20 | | 5.1 | 12.2 | 841 |
| C | A4 | 20 | 80 | | 20 | 3.4 | 11.9 | 912 |
| D | | | 80 | 20 | | 3.2 | 12.8 | 918 |
| E | | | 60 | | 40 | 3.8 | 11.3 | 924 |
| F | | | 60 | 40 | | 3.3 | 13.1 | 948 |
| G | A5 | 30 | 20 | | 80 | 2.16 | 4.75 | 1100 |
| H | | | 20 | 80 | | 3.45 | 9.71 | 1230 |
| I | A7 | 40 | 20 | | 80 | 1.49 | 2.29 | 1000 |
| J | | | 20 | 80 | | 2.14 | 8.90 | 1340 |
| K | A8 | 45 | 20 | | 80 | 2.12 | 4.02 | 1280 |
| L | | | 20 | 80 | | 2.16 | 8.27 | 1360 |

**total plasticizer B concentration (phm) on top of total weight of monomers of block copolymer A or C Table 5 shows that the S-TPE compositions according to the invention have significantly improved mechanical properties while also having a very good softness as indicated by their shore A hardness (cp. Table 2), almost all values are between 60 and 40.

Very good overall results, including the mechanical properties, are obtained with a composition comprising a plasticizer mixture B1/B3. S-TPE compositions comprising 15 to 20 phm of plasticizer B, in particular plasticizer b2) (mixture B1/B3), show a high stress at break (more than 11 MPa) and are very soft (Shore A hardness of 64 to 50).

Compositions comprising 30 to 45 phm of plasticizer B, in particular plasticizer b2) (mixture B1/B3), show a good stress at break (often more than 8 MPa) and a high strain at break (often more than 1200%) and are extremely soft (Shore A hardness of 45 to 38).

Optical Properties and Melt Volume Flow Rate

Samples were prepared—as hereinbefore described—and tested for their optical properties. Additionally the MFI (200° C., 5 kg) of these samples was determined.

Transparency, haze and clarity were measured on a BYK Haze-gard I according to ASTM D1003 on 2 mm compression molded plates which were produced at 200° C. under 40 bar during 10 min.

The data obtained are shown in Table 6.

TABLE 6

| Sample | Block copolymer A | Plasticizer B** (phm) | Fraction of B1 (wt.-%) based on B | Fraction of B3 (wt.-%) based on B | Fraction of B2 (wt.-%) based on B | Transparency (%) | Haze (%) | Clarity (%) | MFI (cm³/10 min) |
|---|---|---|---|---|---|---|---|---|---|
| A | A3 | 15 | 80 | | 20 | 91.3 | 7.8 | 54.0 | 11.9 |
| B | | | 80 | 20 | | 91.0 | 7.9 | 80.5 | 10.7 |

TABLE 6-continued

| Sample | Block copolymer A | Plasticizer B** (phm) | Fraction of B1 (wt.-%), based on B | Fraction of B3 (wt.-%) based on B | Fraction of B2 (wt.-%) based on B | Transparency (%) | Haze (%) | Clarity (%) | MFI (cm³/10 min) |
|---|---|---|---|---|---|---|---|---|---|
| C | A4 | 20 | 80 | | 20 | 91.8 | 5.8 | 77.6 | 7.4 |
| D | | | 80 | 20 | | 91.1 | 8.9 | 75.0 | 8.7 |
| E | | | 60 | | 40 | 91.1 | 8.9 | 75.0 | 8.3 |
| F | | | 60 | 40 | | 87.3 | 11.9 | 83.0 | 10.2 |
| G | A5 | 30 | 20 | | 80 | 90.6 | 19.2 | 77.6 | 15.4 |
| H | | | 20 | 80 | | 91.1 | 12.1 | 74.6 | 4.1 |
| I | A7 | 40 | 20 | | 80 | 89.8 | 29.4 | 50.8 | 16 |
| J | | | 20 | 80 | | 90.7 | 24.1 | 67.4 | 14.9 |
| K | A8 | 45 | 20 | | 80 | 91.8 | 12.7 | 77.6 | 15.8 |
| L | | | 20 | 80 | | 91.0 | 14.0 | 78.1 | 12.7 |

The data as shown in Table 6 prove that the compositions according to the invention have a high transparency. Moreover, the MFI values of the inventive samples obtained are such as to allow good processing, even when increasing amounts (cp. 40, 45 phm) of plasticizer are added.

The invention claimed is:

1. A thermoplastic elastomer composition comprising components a), b), and c):
    a) 90.9 to 69.0 wt.-% of at least one star-shaped block copolymer A of the structure $$[S_1-(S/B)_k-(S/B)_l-(S/B)_m-S_2]_n-X \quad (I),$$

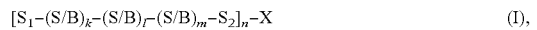

where $S_1$ and $S_2$ are polymer blocks made from at least one vinylaromatic monomer and S/B are random copolymer blocks made from at least one vinylaromatic monomer and at least one diene forming a soft phase; X is a coupling center derived from a polyfunctional coupling agent;
    b) 9.1 to 31.0 wt.-% of a plasticizer B; and
    c) 0 to 2.0 wt.-% of further additives C;
    wherein the sum of components a), b), and c) is 100 wt.-%;
    the arms $S_1-(S/B)_k-(S/B)_m-(S/B)_m-S_2$ are identical;
    the proportion of the blocks $S_1$ and $S_2$ (forming a hard phase), based on the entire block copolymer A, is from 24 to 40 wt.-%;
    the vinylaromatic monomer/diene (=S/B) ratio of all of the blocks (S/B) is from 1/0.45 to 1/2.5;
    the S/B-ratio of the blocks $(S/B)_k$, $(S/B)_l$ and $(S/B)_m$ is different from each other; the S/B-ratio of the blocks $(S/B)_k$ and $(S/B)_m$ is lower than the S/B-ratio of the block(s) $(S/B)_l$;
    the weight ratio of blocks $S_2/S_1$ is from 0.1 to 0.8; and
    the weight average molar mass $M_w$ (determined by GPC according to ISO 16014-3:2012) of the block copolymer A is from 220000 to 450000 g/mol;
    n is a natural number from 1 to 8;
    k and m are 1; and
    l is a natural number of at least 1; and
    the plasticizer B is
        b1) a mixture composed of mineral oil B1 and at least one cyclohexane 1,2-dicarboxylic acid $C_8$ to $C_{10}$ dialkyl ester B2; or
        b2) a mixture composed of mineral oil B1 and at least one vegetable oil B3 having an iodine value (g/100 g) of no more than 130.

2. The thermoplastic elastomer composition according to claim 1, wherein the plasticizer in plasticizer mixture b1) or b2) the weight ratio of component B1 to component B2 or B1 to B3 is 80:20 to 40:60.

3. The thermoplastic elastomer composition according to claim 1, wherein the plasticizer B is mixture b2).

4. The thermoplastic elastomer composition according to claim 1, wherein the vegetable oil B3 is selected from the group consisting of: rapeseed oil, sunflower oil, grape seed oil, palm oil, olive oil, coconut oil, palm kernel oil, cocoa butter, jojoba oil, cottonseed oil, corn oil, wheat germ oil, soybean oil, peanut oil, castor oil, sesame oil, and rice brain oil.

5. The thermoplastic elastomer composition according to claim 1, wherein the vegetable oil B3 is rapeseed oil.

6. The thermoplastic elastomer composition according to claim 1, which melt mass flow index (measured on a polymer melt at 200° C. and 5 kg load according to ISO 1133-1:2011) is in the range of from 8 to 16 cm³/10 min.

7. The thermoplastic elastomer composition according to claim 1 comprising 9.1 to 20.0 wt.-% of plasticizer B (component b)) and the Mw of block copolymer A is 250000 to 320000 g/mol.

8. The thermoplastic elastomer composition according to claim 1 comprising more than 20 wt.-% of plasticizer B (component b)) and the Mw of block copolymer A is 325000 to 410000 g/mol.

9. The thermoplastic elastomer composition according to claim 1, wherein n is a natural number from 3 to 5.

10. The thermoplastic elastomer composition according to claim 1, wherein X is a coupling center derived from epoxidized linseed oil or epoxidized soybean oil.

11. The thermoplastic elastomer composition according to claim 1, wherein Mw of the polymer block $S_1$ is in the range of from 22900 to 54000 g/mol, and Mw of the polymer block $S_2$ is in the range of from 5000 to 12000 g/mol.

12. The thermoplastic elastomer composition according to claim 1, wherein the weight ratio of blocks $S_2/S_1$ of block copolymer A is from 0.1 to 0.6.

13. The thermoplastic elastomer composition according to claim 1, wherein the S/B-ratio of the copolymer block $(S/B)_k$ is from 0.5 to 1.0; the S/B-ratio of the copolymer block(s) $(S/B)_l$ is from 0.5 to 1.2; and the S/B-ratio of the copolymer block $(S/B)_m$ is from 0.3 to 0.8.

14. The thermoplastic elastomer composition according to claim 1, wherein the weight average molar mass $M_w$ of the copolymer blocks $(S/B)_k$, $(S/B)_l$ and $(S/B)_m$ is different from each other;
    Mw $(S/B)_k$ is in the range of from 16500 to 40000 g/mol;
    Mw $(S/B)_l$ is in the range of from 25800 to 60800 g/mol; and Mw $(S/B)_m$ is in the range of from 14300 to 33800 g/mol.

15. A process for the preparation of a thermoplastic elastomer composition according to claim 1, wherein component a) is introduced continuously into an extruder and then component b) and optionally further components c) are metered in.

16. A process for the preparation of a thermoplastic elastomer composition according to claim 1, wherein component b) and optional component c)—as such or in solution—are added into a solution of block copolymer A, then to homogenize the liquids, and subsequently to free the product from the solvent.

17. A shaped article produced from the thermoplastic elastomer composition according to claim 1.

18. A star-shaped block copolymer A of the structure

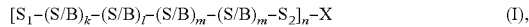

$$[S_1-(S/B)_k-(S/B)_l-(S/B)_m-(S/B)_m-S_2]_n-X \quad (I),$$

wherein:
- $S_1$ and $S_2$ are polymer blocks made from at least one vinylaromatic monomer and S/B are random copolymer blocks made from at least one vinylaromatic monomer and at least one diene forming a soft phase;
- X is a coupling center derived from a polyfunctional coupling agent;
- the arms $S_1-(S/B)_k-(S/B)_m-(S/B)_m-S_2$ are identical;
- the proportion of the blocks $S_1$ and $S_2$ (forming a hard phase), based on the entire block copolymer A, is from 24 to 40 wt.-%;
- the vinylaromatic monomer/diene (=S/B) ratio of all of the blocks (S/B) is from 1/0.45 to 1/2.5;
- the S/B-ratio of the blocks $(S/B)_k$, $(S/B)_l$, and $(S/B)_m$ is different from each other;
- the S/B-ratio of the blocks $(S/B)_k$ and $(S/B)_m$ is lower than the S/B-ratio of the block(s) $(S/B)_l$;
- the weight ratio of blocks $S_2/S_1$ is from 0.1 to 0.8;
- the weight average molar mass $M_w$ (determined by GPC according to ISO 16014-3:2012) of the block copolymer A is from 220000 to 450000 g/mol;
- n is a natural number from 1 to 8;
- k and m are 1; and
- l is a natural number of at least 1.

19. A process for the preparation of block copolymer A of formula (I) according to claim 18 characterized by
- i) a single initiation;
- ii) first addition and polymerization of vinyl aromatic monomer;
- iii) at least 3 times addition and polymerization of vinyl aromatic monomer and diene mixture;
- iv) second addition and polymerization of vinyl aromatic monomer; and
- v) a coupling step after the addition and polymerization of the vinylaromatic monomers of the last polymer block.

20. The shaped article of claim 17, wherein the shaped article is a medical article.

21. The shaped article of claim 20, wherein the medical article is for skin contact applications or intravenous applications.

22. An elastic and flexible molding produced from the thermoplastic elastomer composition according to claim 1.

* * * * *